United States Patent
Nardi et al.

(10) Patent No.: US 8,101,649 B2
(45) Date of Patent: Jan. 24, 2012

(54) N-ACYLHYDRAZONE DERIVATIVES USEFUL AS MODULATORS OF NICOTINIC ACETYLCHOLINE RECEPTORS

(75) Inventors: Antonio Nardi, Herzogenrath (DE); Jeppe Kejser Christensen, København N (DK); Dan Peters, Malmö (SE); Tino Dyhring, Solrød (DK)

(73) Assignee: Neurosearch A/S, Ballerup (DK)

( * ) Notice: Subject to any disclaimer, the term of this patent is extended or adjusted under 35 U.S.C. 154(b) by 0 days.

(21) Appl. No.: 12/743,836

(22) PCT Filed: Nov. 19, 2008

(86) PCT No.: PCT/EP2008/065830
§ 371 (c)(1),
(2), (4) Date: Jul. 20, 2010

(87) PCT Pub. No.: WO2009/065854
PCT Pub. Date: May 28, 2009

(65) Prior Publication Data
US 2010/0280092 A1    Nov. 4, 2010

Related U.S. Application Data

(60) Provisional application No. 60/990,162, filed on Nov. 26, 2007.

(30) Foreign Application Priority Data

Nov. 21, 2007  (DK) ................................. 2007 01658

(51) Int. Cl.
| | |
|---|---|
| *A61K 31/405* | (2006.01) |
| *C07D 209/20* | (2006.01) |
| *A61P 25/00* | (2006.01) |
| *A61P 25/28* | (2006.01) |
| *A61P 25/24* | (2006.01) |
| *A61P 25/22* | (2006.01) |
| *A61P 9/12* | (2006.01) |
| *A61P 9/06* | (2006.01) |
| *A61P 29/00* | (2006.01) |
| *A61P 25/30* | (2006.01) |

(52) U.S. Cl. ........................................ 514/419; 548/494
(58) Field of Classification Search ........................ None
See application file for complete search history.

(56) References Cited

FOREIGN PATENT DOCUMENTS
WO    WO 2007/056159 A2    5/2007

OTHER PUBLICATIONS

Bryant et al., caplus an 2007:537999.*
Mndzhoyan et al., caplus an 1960:62672.*
Alzheimer's Disease Treatment Phases, http://www.alzheimerstreatment.org/treatment/disease-treatment.htm.*
Alzheimer's Drugs, Consumer Reports Best Buy Drugs (p. 1-5).*
Patani et al., Chem. Rev., 1996, 96, 3147-3176.*
Alemany et al., caplus an 1967:443621.*
Elderfield et al., "Synthesis of Potential Anticancer Agents. XV. Nitrogen Mustards from Indole Derivatives", Journal of Organic Chemistry, vol. 27, pp. 2463-2465, Jul. 1962. ISSN: 0022-3263 XP002514325.

* cited by examiner

*Primary Examiner* — Sun Jae Loewe
(74) *Attorney, Agent, or Firm* — Birch, Stewart, Kolasch & Birch, LLP

(57) ABSTRACT

This invention relates to N-acylhydrazone derivatives, which are found to be useful as modulators of the nicotinic acetylcholine receptors. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

11 Claims, 1 Drawing Sheet

N-ACYLHYDRAZONE DERIVATIVES USEFUL AS MODULATORS OF NICOTINIC ACETYLCHOLINE RECEPTORS

This application is the National Phase of PCT/EP2008/065830 filed on Nov. 19, 2008, which claims priority under 35 U.S.C. 119(e) to U.S. Provisional Application No. 60/990,162 filed on Nov. 26, 2007 and under 35 U.S.C. 119(a) to patent application Ser. No. PA 2007 01658 filed in Denmark on Nov. 21, 2007, all of which are hereby expressly incorporated by reference into the present application.

TECHNICAL FIELD

This invention relates to N-acylhydrazone derivatives, which are found to be useful as modulators of the nicotinic acetylcholine receptors. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

BACKGROUND ART

The endogenous cholinergic neurotransmitter, acetylcholine, exert its biological effect via two types of cholinergic receptors, the muscarinic Acetyl Choline Receptors (mAChR) and the nicotinic Acetyl Choline Receptors (nAChR).

As it is well established that muscarinic acetylcholine receptors dominate quantitatively over nicotinic acetylcholine receptors in the brain area important to memory and cognition, and much research aimed at the development of agents for the treatment of memory related disorders have focused on the synthesis of muscarinic acetylcholine receptor modulators.

Recently, however, an interest in the development of nAChR modulators has emerged. Several diseases are associated with degeneration of the cholinergic system i.e. senile dementia of the Alzheimer type, vascular dementia and cognitive impairment due to the organic brain damage disease related directly to alcoholism.

SUMMARY OF THE INVENTION

The present invention is devoted to the provision novel modulators of the nicotinic receptors, which modulators are useful for the treatment of diseases or disorders related to the cholinergic receptors, and in particular the nicotinic acetylcholine α7 receptor subtype.

The compounds of the invention may also be useful as diagnostic tools or monitoring agents in various diagnostic methods, and in particular for in vivo receptor imaging (neuroimaging), and they may be used in labelled or unlabelled form.

In its first aspect the invention relates to the use of certain N-acylhydrazone derivatives represented by Formula I

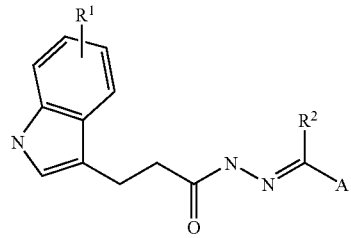

a stereoisomer thereof or a mixture of its stereoisomers, or a pharmaceutically acceptable salt thereof, wherein A represents a cycloalkyl group; a phenyl group optionally substituted with one or more substituents selected from alkyl, halo, trifluoromethyl, cyano, hydroxy and alkoxy; or a furanyl or a thienyl group; or A together with $R^2$, together with the carbon atom to which they are attached, form a naphthalene or hydrogenated naphthalene ring, which naphthalene and hydrogenated naphthalene are optionally substituted one or more times with substituents selected from alkyl and oxo;

$R^1$ represents hydrogen, halo or trifluoromethyl; and $R^2$ represents hydrogen or alkyl; or $R^2$ together with A, and together with the carbon atom to which they are attached, form a naphthalene or hydrogenated naphthalene ring, which naphthalene and hydrogenated naphthalene are optionally substituted one or more times with substituents selected from alkyl and oxo;

as medicaments for the treatment, prevention or alleviation of a disease or a disorder or a condition of a mammal, including a human, which disease, disorder or condition is responsive to modulation of nicotinic acetylcholine receptors.

In a second aspect the invention provides novel N-acylhydrazone derivatives represented by Formula I

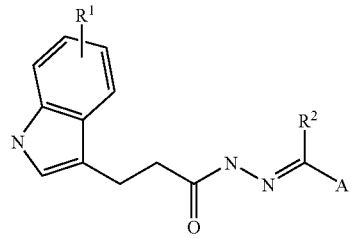

a stereoisomer thereof or a mixture of its stereoisomers, or a pharmaceutically acceptable salt thereof, wherein $R^1$ represents halo or trifluoromethyl; and A represents a cycloalkyl group; a phenyl group optionally substituted with one or more substituents selected from alkyl, halo, trifluoromethyl, cyano, hydroxy and alkoxy; or a furanyl or a thienyl group; or A together with $R^2$, together with the carbon atom to which they are attached, form a naphthalene or hydrogenated naphthalene ring, which naphthalene and hydrogenated naphthalene are optionally substituted one or more times with substituents selected from alkyl and oxo; or $R^1$ represents hydrogen; and A represents a cycloalkyl group; a phenyl group substituted with one or more substituents selected from alkyl, halo, trifluoromethyl, cyano, hydroxy and alkoxy; or a furanyl or a thienyl group; or A together with $R^2$, together with the carbon atom to which they are attached, form a naphthalene or hydrogenated naphthalene ring, which naphthalene and hydrogenated naphthalene are optionally substituted one or more times with substituents selected from alkyl and oxo; and $R^2$ represents hydrogen or alkyl; or $R^2$ together with A, and together with the carbon atom to which they are attached, form a naphthalene or hydrogenated naphthalene ring, which naphthalene and hydrogenated naphthalene are optionally substituted one or more times with substituents selected from alkyl and oxo.

In a third aspect the invention provides pharmaceutical compositions comprising a therapeutically effective amount of the N-acylhydrazone derivative of the invention, or a pharmaceutically-acceptable addition salt thereof, together with at least one pharmaceutically-acceptable carrier or diluent.

Viewed from another aspect the invention relates to the use of the N-acylhydrazone derivative of the invention, or a pharmaceutically-acceptable addition salt thereof, for the manufacture of pharmaceutical compositions/medicaments for the treatment, prevention or alleviation of a disease or a disorder or a condition of a mammal, including a human, which disease, disorder or condition is responsive to modulation of cholinergic receptors.

In yet another aspect the invention provides a method for treatment, prevention or alleviation of diseases, disorders or conditions of a living animal body, including a human, which disorder, disease or condition is responsive to modulation of cholinergic receptors, and which method comprises the step of administering to such a living animal body in need thereof a therapeutically effective amount of the N-acylhydrazone derivative of the invention.

Other objects of the invention will be apparent to the person skilled in the art from the following detailed description and examples.

DETAILED DISCLOSURE OF THE INVENTION

N-acylhydrazone Derivatives for Medical Use

In its first aspect the invention relates to the use of certain N-acylhydrazone derivatives as pharmaceutical ingredients for use as medicaments for combating diseases, disorders or conditions that are responsive to modulation of nicotinic acetylcholine receptors.

The N-acylhydrazone derivatives for use according to the invention may be characterized by Formula I

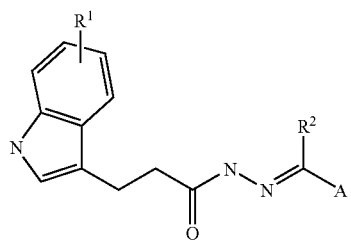

(I)

a stereoisomer thereof or a mixture of its stereoisomers, or a pharmaceutically acceptable salt thereof, wherein A represents a cycloalkyl group; a phenyl group optionally substituted with one or more substituents selected from alkyl, halo, trifluoromethyl, cyano, hydroxy and alkoxy; or a furanyl or a thienyl group; or A together with $R^2$, together with the carbon atom to which they are attached, form a naphthalene or hydrogenated naphthalene ring, which naphthalene and hydrogenated naphthalene are optionally substituted one or more times with substituents selected from alkyl and oxo;

$R^1$ represents hydrogen, halo or trifluoromethyl; and $R^2$ represents hydrogen or alkyl; or $R^2$ together with A, and together with the carbon atom to which they are attached, form a naphthalene or hydrogenated naphthalene ring, which naphthalene and hydrogenated naphthalene are optionally substituted one or more times with substituents selected from alkyl and oxo.

In a preferred embodiment the N-acylhydrazone derivative for use according to the invention is a compound of Formula I, a stereoisomer thereof or a mixture of its stereoisomers, or a pharmaceutically acceptable salt thereof, wherein A represents a cycloalkyl group; a phenyl group optionally substituted with one or more substituents selected from alkyl, halo, trifluoromethyl, cyano, hydroxy and alkoxy; or a furanyl or a thienyl group.

In a more preferred embodiment A represents a cycloalkyl group.

In another more preferred embodiment A represents a phenyl group optionally substituted with one or more substituents selected from alkyl, halo, trifluoromethyl, cyano, hydroxy and alkoxy.

In a third more preferred embodiment A represents a phenyl group optionally substituted with halo, trifluoromethyl, cyano, hydroxy or alkoxy.

In a fourth more preferred embodiment A represents a phenyl group optionally substituted with halo or alkoxy.

In a fifth more preferred embodiment A represents a phenyl group substituted with halo, and in particular fluoro or chloro.

In a sixth more preferred embodiment A represents a phenyl group substituted with alkoxy, and in particular methoxy.

In a seventh more preferred embodiment A represents a phenyl group.

In an eight more preferred embodiment A represents a furanyl or a thienyl group.

In a ninth more preferred embodiment A represents a furanyl group.

In a tenth more preferred embodiment A represents a thienyl group.

In another preferred embodiment the N-acylhydrazone derivative for use according to the invention is a compound of Formula I, a stereoisomer thereof or a mixture of its stereoisomers, or a pharmaceutically acceptable salt thereof, wherein A with $R^2$, together with the carbon atom to which they are attached, form a naphthalene or hydrogenated naphthalene ring, which naphthalene and hydrogenated naphthalene are optionally substituted one or more times with substituents selected from alkyl and oxo.

In a more preferred embodiment A and $R^2$ form a 3,4-dihydro-2H-naphthalenyl group.

In another more preferred embodiment A and $R^2$ form a 3-methyl-4-oxo-4H-naphthalenyl group.

In a third preferred embodiment the N-acylhydrazone derivative for use according to the invention is a compound of Formula I, a stereoisomer thereof or a mixture of its stereoisomers, or a pharmaceutically acceptable salt thereof, wherein $R^1$ represents hydrogen, halo or trifluoromethyl.

In a more preferred embodiment $R^1$ represents hydrogen or halo, and in particular fluoro.

In another more preferred embodiment $R^1$ represents hydrogen.

In a third more preferred embodiment $R^1$ represents halo, and in particular fluoro.

In a fourth preferred embodiment the N-acylhydrazone derivative for use according to the invention is a compound of Formula I, a stereoisomer thereof or a mixture of its stereoisomers, or a pharmaceutically acceptable salt thereof, wherein $R^2$ represents hydrogen or alkyl.

In a more preferred embodiment R² represents hydrogen.

In another more preferred embodiment R² represents alkyl, and in particular methyl.

In a third more preferred embodiment R² together with A, and together with the carbon atom to which they are attached, form a naphthalene or hydrogenated naphthalene ring, which naphthalene and hydrogenated naphthalene are optionally substituted one or more times with substituents selected from alkyl and oxo.

In a fourth more preferred embodiment wherein R² together with A form a 3,4-dihydro-2H-naphthalenyl group.

In a fifth more preferred embodiment wherein R² together with A form a 3-methyl-4-oxo-4H-naphthalenyl group.

In a most preferred embodiment the N-acylhydrazone derivative for use according to the invention is 3-(1H-Indol-3-yl)-propionic acid [1-(4-fluoro-phenyl)-meth-(E)-ylidene]-hydrazide;
3-(1H-Indol-3-yl)-propionic acid [1-phenyl-meth-(E)-ylidene]-hydrazide;
3-(1H-Indol-3-yl)-propionic acid [1-(4-methoxy-phenyl)-meth-(E)-ylidene]-hydrazide;
3-(1H-Indol-3-yl)-propionic acid [1-(3-fluoro-phenyl)-meth-(E)-ylidene]-hydrazide;
3-(1H-Indol-3-yl)-propionic acid [1-thiophen-3-yl-meth-(E)-ylidene]-hydrazide;
3-(1H-Indol-3-yl)-propionic acid [1-(2-fluoro-phenyl)-meth-(E)-ylidene]-hydrazide;
3-(1H-Indol-3-yl)-propionic acid [1-thiophen-2-yl-meth-(E)-ylidene]-hydrazide;
3-(1H-Indol-3-yl)-propionic acid [1-(4-chloro-phenyl)-meth-(E)-ylidene]-hydrazide;
3-(1H-Indol-3-yl)-propionic acid [1-cyclohexyl-meth-(E)-ylidene]-hydrazide;
3-(5-Fluoro-1H-indol-3-yl)-propionic acid [1-phenyl-meth-(E)-ylidene]-hydrazide;
3-(5-Fluoro-1H-indol-3-yl)-propionic acid [1-(2-fluoro-phenyl)-meth-(E)-ylidene]-hydrazide;
3-(1H-Indol-3-yl)-propionic acid [1-phenyl-eth-(E)-ylidene]-hydrazide;
3-(1H-Indol-3-yl)-propionic acid [3,4-dihydro-2H-naphthalen-(1E)-ylidene]-hydrazide;
3-(5-Fluoro-1H-indol-3-yl-propionic acid [1-(4-fluoro-phenyl)-meth-(E)-ylidene]-hydrazide; or
3-(1H-Indol-3-yl)-propionic acid [3-methyl-4-oxo-4H-naphthalen-(1Z)-ylidene]-hydrazide;

a stereoisomer thereof or a mixture of its stereoisomers, or a pharmaceutically acceptable salt thereof.

N-acylhydrazone Derivatives of the Invention

In a second aspect the invention provides novel N-acylhydrazone derivatives represented by Formula I

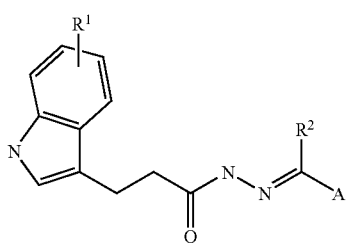

(I)

a stereoisomer thereof or a mixture of its stereoisomers, or a pharmaceutically acceptable salt thereof, wherein R¹ represents halo or trifluoromethyl; and A represents a cycloalkyl group; a phenyl group optionally substituted with one or more substituents selected from alkyl, halo, trifluoromethyl, cyano, hydroxy and alkoxy; or a furanyl or a thienyl group; or A together with R², together with the carbon atom to which they are attached, form a naphthalene or hydrogenated naphthalene ring, which naphthalene and hydrogenated naphthalene are optionally substituted one or more times with substituents selected from alkyl and oxo; or R¹ represents hydrogen; and A represents a cycloalkyl group; a phenyl group substituted with one or more substituents selected from alkyl, halo, trifluoromethyl, cyano, hydroxy and alkoxy; or a furanyl or a thienyl group; or A together with R², together with the carbon atom to which they are attached, form a naphthalene or hydrogenated naphthalene ring, which naphthalene and hydrogenated naphthalene are optionally substituted one or more times with substituents selected from alkyl and oxo; and R² represents hydrogen or alkyl; or R² together with A, and together with the carbon atom to which they are attached, form a naphthalene or hydrogenated naphthalene ring, which naphthalene and hydrogenated naphthalene are optionally substituted one or more times with substituents selected from alkyl and oxo.

In a preferred embodiment the N-acylhydrazone derivative of the invention is a compound of Formula I, a stereoisomer thereof or a mixture of its stereoisomers, or a pharmaceutically acceptable salt thereof, wherein R¹ represents halo or trifluoromethyl; and
A represents
a cycloalkyl group;
a phenyl group optionally substituted with one or more substituents selected from alkyl, halo, trifluoromethyl, cyano, hydroxy and alkoxy; or
a furanyl or a thienyl group;
or A together with R², together with the carbon atom to which they are attached, form a naphthalene or hydrogenated naphthalene ring, which naphthalene and hydrogenated naphthalene are optionally substituted one or more times with substituents selected from alkyl and oxo.

In a more preferred embodiment R¹ represents halo, and in particular fluoro, or trifluoromethyl.

In another more preferred embodiment A represents a cycloalkyl group; a phenyl group optionally substituted with one or more substituents selected from alkyl, halo, trifluoromethyl, cyano, hydroxy and alkoxy; or a furanyl or a thienyl group.

In a third more preferred embodiment A represents a cycloalkyl group, and in particular cyclohexyl.

In a fourth more preferred embodiment A represents a phenyl group optionally substituted with one or more substituents selected from alkyl, halo, trifluoromethyl, cyano, hydroxy and alkoxy.

In a fifth more preferred embodiment A represents a furanyl or a thienyl group.

In a sixth more preferred embodiment A together with R², together with the carbon atom to which they are attached, form a naphthalene or hydrogenated naphthalene ring, which naphthalene and hydrogenated naphthalene are optionally substituted one or more times with substituents selected from alkyl and oxo.

In a seventh more preferred embodiment A together with R², together with the carbon atom to which they are attached, form a 3,4-dihydro-2H-naphthalene ring.

In an eight more preferred embodiment A together with R², together with the carbon atom to which they are attached, form a 3-methyl-4-oxo-4H-naphthalene ring.

In another preferred embodiment the N-acylhydrazone derivative of the invention is a compound of Formula I, a stereoisomer thereof or a mixture of its stereoisomers, or a pharmaceutically acceptable salt thereof, wherein $R^1$ represents hydrogen; and A represents a cycloalkyl group; a phenyl group substituted with one or more substituents selected from alkyl, halo, trifluoromethyl, cyano, hydroxy and alkoxy; or a furanyl or a thienyl group; or A together with $R^2$, together with the carbon atom to which they are attached, form a naphthalene or hydrogenated naphthalene ring, which naphthalene and hydrogenated naphthalene are optionally substituted one or more times with substituents selected from alkyl and oxo.

In a more preferred embodiment A represents a cycloalkyl group, and in particular cyclohexyl.

In another more preferred embodiment A represents a phenyl group substituted with one or more substituents selected from alkyl, halo, trifluoromethyl, cyano, hydroxy and alkoxy.

In a third more preferred embodiment A represents a phenyl group substituted once or twice with substituents selected from halo, trifluoromethyl and cyano.

In a fourth more preferred embodiment A represents a phenyl group substituted with halo, trifluoromethyl or cyano.

In a fifth more preferred embodiment A represents a phenyl group substituted with halo, and in particular fluoro.

In a sixth more preferred embodiment A represents a furanyl or a thienyl group.

In a seventh more preferred embodiment A together with $R^2$, together with the carbon atom to which they are attached, form a naphthalene or hydrogenated naphthalene ring, which naphthalene and hydrogenated naphthalene are optionally substituted one or more times with substituents selected from alkyl and oxo.

In a third preferred embodiment the N-acylhydrazone derivative of the invention is a compound of Formula I, a stereoisomer thereof or a mixture of its stereoisomers, or a pharmaceutically acceptable salt thereof, wherein $R^2$ represents hydrogen or alkyl.

In a fourth preferred embodiment the N-acylhydrazone derivative of the invention is a compound of Formula I, a stereoisomer thereof or a mixture of its stereoisomers, or a pharmaceutically acceptable salt thereof, wherein $R^2$ together with A, and together with the carbon atom to which they are attached, form a naphthalene or hydrogenated naphthalene ring, which naphthalene and hydrogenated naphthalene are optionally substituted one or more times with substituents selected from alkyl, and in particular methyl, and oxo.

In a more preferred embodiment A together with $R^2$, together with the carbon atom to which they are attached, form a naphthalene or hydrogenated naphthalene ring, which naphthalene and hydrogenated naphthalene are optionally substituted one or more times with substituents selected from alkyl and oxo.

In another more preferred embodiment A together with $R^2$, together with the carbon atom to which they are attached, form a 3,4-dihydro-2H-naphthalene ring.

In a third more preferred embodiment A together with $R^2$, together with the carbon atom to which they are attached, form a 3-methyl-4-oxo-4H-naphthalene ring.

In a most preferred embodiment the N-acylhydrazone derivative of the invention is 3-(1H-Indol-3-yl)-propionic acid [1-thiophen-3-yl-meth-(E)-ylidene]-hydrazide;

3-(1H-Indol-3-yl)-propionic acid [1-cyclohexyl-meth-(E)-ylidene]-hydrazide;

3-(5-Fluoro-1H-indol-3-yl)-propionic acid [1-phenyl-meth-(E)-ylidene]-hydrazide;

3-(5-Fluoro-1H-indol-3-yl)-propionic acid [1-(2-fluoro-phenyl)-meth-(E)-ylidene]-hydrazide;

3-(1H-Indol-3-yl)-propionic acid [3,4-dihydro-2H-naphthalen-(1E)-ylidene]-hydrazide;

3-(5-Fluoro-1H-indol-3-yl)-propionic acid [1-(4-fluoro-phenyl)-meth-(E)-ylidene]-hydrazide; or 3-(1H-Indol-3-yl)-propionic acid [3-methyl-4-oxo-4H-naphthalen-(1Z)-ylidene]-hydrazide;

a stereoisomer thereof or a mixture of its stereoisomers, or a pharmaceutically acceptable salt thereof.

Any combination of two or more of the embodiments described herein is considered within the scope of the present invention.

Definition of Substituents

In the context of this invention halo represents fluoro, chloro, bromo or iodo.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention an alkoxy group designates an "alkyl-O-" group, wherein alkyl is as defined above. Examples of preferred alkoxy groups of the invention include methoxy and ethoxy.

Pharmaceutically Acceptable Salts

The N-acylhydrazone derivative of the invention may be provided in any form suitable for the intended administration. Suitable forms include pharmaceutically (i.e. physiologically) acceptable salts, and pre- or prodrug forms of the compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Metal salts of an N-acylhydrazone derivative of the invention include alkali metal salts, such as the sodium salt of a compound of the invention containing a carboxy group.

Steric Isomers

It will be appreciated by those skilled in the art that the N-acylhydrazone derivatives of the present invention may exist in different stereoisomeric forms, including enantiomers, diastereomers, as well as geometric isomers (cis-trans isomers). The invention includes all such stereoisomers and any mixtures thereof including racemic mixtures.

Racemic forms can be resolved into the optical antipodes by known methods and techniques. One way of separating the enantiomeric compounds (including enantiomeric intermediates) is—in the case the compound being a chiral acid by use of an optically active amine, and liberating the diastereomeric, resolved salt by treatment with an acid. Another method for resolving racemates into the optical antipodes is based upon chromatography on an optical active matrix. Racemic compounds of the present invention can thus be resolved into their optical antipodes, e.g., by fractional crystallisation of D- or L- (tartrates, mandelates, or camphorsulphonate) salts for example.

Additional methods for the resolving the optical isomers are known in the art. Such methods include those described by Jaques J, Collet A, & Wilen S in "Enantiomers, Racemates, and Resolutions", John Wiley and Sons, New York (1981).

Optical active compounds can also be prepared from optically active starting materials or intermediates.

Methods of Producing N-acylhydrazone Derivatives

The N-acylhydrazone derivative of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The present invention is devoted to the provision novel modulators of the nicotinic receptors, which modulators are useful for the treatment of diseases or disorders related to the cholinergic receptors, and in particular the nicotinic acetylcholine receptor (nAChR). Preferred compounds of the invention show activity as positive modulators of the nicotinic acetylcholine $\alpha 7$ receptor subtype.

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

The compounds of the invention may also be useful as diagnostic tools or monitoring agents in various diagnostic methods, and in particular for in vivo receptor imaging (neuroimaging), and they may be used in labelled or unlabelled form.

In a preferred embodiment the disease, disorder or condition contemplated according to the invention, and responsive to modulation of nicotinic acetylcholine receptors is anxiety, a cognitive disorder, a learning deficit, a memory deficit or dysfunction, Alzheimer's disease, attention deficit, attention deficit hyperactivity disorder, Parkinson's disease, Huntington's disease, Amyotrophic Lateral Sclerosis, Gilles de la Tourette's syndrome, depression, mania, manic depression, psychosis, schizophrenia, obsessive compulsive disorders (OCD), panic disorders, an eating disorder including anorexia nervosa, bulimia and obesity, narcolepsy, nociception, AIDS-dementia, senile dementia, peripheral neuropathy, autism, dyslexia, tardive dyskinesia, hyperkinesia, epilepsy, post-traumatic syndrome, social phobia, a sleeping disorder, pseudodementia, Ganser's syndrome, pre-menstrual syndrome, late luteal phase syndrome, chronic fatigue syndrome, mutism, trichotillomania, jet-lag, hypertension, cardiac arrhythmias, a smooth muscle contraction disorder including convulsive disorders, angina pectoris, premature labour, convulsions, diarrhoea, asthma, epilepsy, tardive dyskinesia, hyperkinesia, premature ejaculation and erectile difficulty, an endocrine system disorder including thyrotoxicosis and pheochromocytoma, a neurodegenerative disorder, including transient anoxia and induced neuro-degeneration, pain, mild, moderate or severe pain, acute pain, chronic pain, pain of recurrent character, neuropathic pain, pain caused by migraine, postoperative pain, phantom limb pain, neuropathic pain, chronic headache, central pain, pain related to diabetic neuropathy, to postherpetic neuralgia or to peripheral nerve injury, an inflammatory disorder, including an inflammatory skin disorder, acne, rosacea, Crohn's disease, inflammatory bowel disease, ulcerative colitis and diarrhoea, a disorder associated with drawal symptoms caused by termination of use of addictive substances, including nicotine withdrawal symptoms, opioid withdrawal symptoms including heroin, cocaine and morphine, benzodiazepine withdrawal symptoms including benzodiazepine-like drugs and alcohol.

In a more preferred embodiment the disease, disorder or condition responsive to modulation of nicotinic acetylcholine receptors is a cognitive disorder, psychosis, schizophrenia or depression.

In another more preferred embodiment the disease, disorder or condition responsive to modulation of nicotinic acetylcholine receptors is associated with smooth muscle contractions, including convulsive disorders, angina pectoris, premature labour, convulsions, diarrhoea, asthma, epilepsy, tardive dyskinesia, hyperkinesia, premature ejaculation and erectile difficulty.

In still another more preferred embodiment the disease, disorder or condition responsive to modulation of nicotinic acetylcholine receptors is related to the endocrine system, such as thyrotoxicosis and pheochromocytoma.

In yet another more preferred embodiment the disease, disorder or condition responsive to modulation of nicotinic acetylcholine receptors is a neurodegenerative disorder including transient anoxia and induced neuro-degeneration.

In a further more preferred embodiment the disease, disorder or condition responsive to modulation of nicotinic acetylcholine receptors is pain, including mild, moderate or even severe pain of acute, chronic or recurrent character, as well as pain caused by migraine, postoperative pain, and phantom limb pain. The pain may in particular be neuropathic pain, chronic headache, central pain, pain related to diabetic neuropathy, to postherpetic neuralgia, or to peripheral nerve injury.

In a further more preferred embodiment the disease, disorder or condition responsive to modulation of nicotinic acetylcholine receptors is an inflammatory skin disorder such as acne and rosacea, Crohn's disease, inflammatory bowel disease, ulcerative colitis, and diarrhoea.

Finally the compounds of the invention may be useful for the treatment of withdrawal symptoms caused by termination of use of addictive substances. Such addictive substances include nicotine containing products such as tobacco, opioids such as heroin, cocaine and morphine, benzodiazepines and benzodiazepine-like drugs, and alcohol. Withdrawal from addictive substances is in general a traumatic experience characterised by anxiety and frustration, anger, anxiety, difficulties in concentrating, restlessness, decreased heart rate and increased appetite and weight gain.

In this context "treatment" covers treatment, prevention, prophylactics and alleviation of withdrawal symptoms and abstinence as well as treatment resulting in a voluntary diminished intake of the addictive substance.

Pharmaceutical Compositions

In another aspect the invention provides novel pharmaceutical compositions comprising a therapeutically effective amount of N-acylhydrazone derivative of the invention.

While an N-acylhydrazone derivative of the invention for use in therapy may be administered in the form of the raw compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the N-acylhydrazone derivative of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be manufactured by the skilled person by use of standard methods and conventional techniques appropriate to the desired formulation. When desired, compositions adapted to give sustained release of the active ingredient may be employed.

Further details on techniques for formulation and administration may be found in the latest edition of Remington's Pharmaceutical Sciences (Maack Publishing Co., Easton, Pa.).

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

The N-acylhydrazone derivatives of the present invention are valuable nicotinic receptor modulators, and therefore useful for the treatment of a range of ailments involving cholinergic dysfunction as well as a range of disorders responsive to the action of nAChR modulators.

In another aspect the invention provides a method for the treatment, prevention or alleviation of a disease or a disorder or a condition of a living animal body, including a human, which disease, disorder or condition is responsive to modulation of cholinergic receptors, and which method comprises administering to such a living animal body, including a human, in need thereof an effective amount of an N-acylhydrazone derivative of the invention.

In the context of this invention the term "treatment" covers treatment, prevention, prophylaxis or alleviation, and the term "disease" covers illnesses, diseases, disorders and conditions related to the disease in question.

The preferred indications contemplated according to the invention are those stated above.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

A satisfactory result can, in certain instances, be obtained at a dosage as low as 0.005 mg/kg i.v. and 0.01 mg/kg p.o. The upper limit of the dosage range is about 10 mg/kg i.v. and 100 mg/kg p.o. Preferred ranges are from about 0.001 to about 1 mg/kg i.v. and from about 0.1 to about 10 mg/kg p.o.

BRIEF DESCRIPTION OF THE DRAWING

The present invention is further illustrated by reference to the accompanying drawing, in which

FIG. 1A shows current traces induced by 100 µM acetylcholine in the absence and in the presence of 0.01 to 31.6 µM of Compound 3;

FIG. 1B shows the concentration-response relationship for the positive modulation of 100 µM acetylcholine responses induced by Compound 3; i.e. % modulation of control vs. log [c] (M). The calculated $EC_{50}$-value is 4.1 µM and the maximal modulation of the acetylcholine response is 140%.

EXAMPLES

Figure 1A:
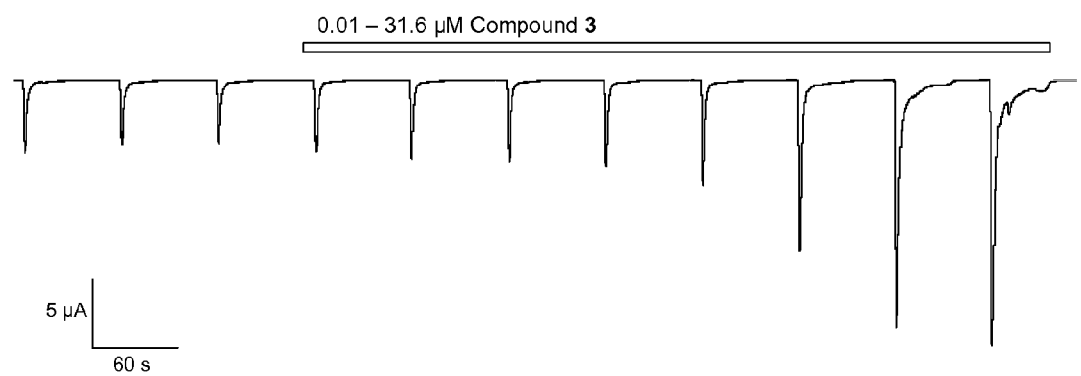
FIGS. 1A and 1B show the modulatory effect of Compound 3 (i.e. 3-(1H-Indol-3-yl)-propionic acid [1-(4-fluoro-phenyl)-meth-(E)-ylidene]-hydrazide) on acetylcholine currents induced in nAChR α7 receptors expressed in *Xenopus* Oocytes.

The invention is further illustrated with reference to the following examples, which are not intended to be in any way limiting to the scope of the invention as claimed.

Example 1

Preparatory Example

General Experimental Procedure

Chemical synthesis of the N-acylhydrazones (V) of the invention is outlined in Scheme 1, below, and involves in the final step the condensation between 1 equivalent of the suitably-synthesised 3-(1H-indol-3-yl)-propionic acid hydrazide (III) and 1 equivalent of the opportune commercial ketone or aldehyde (IV), which is carried out by reflux in toluene for 12-24 hours. The 3-(1H-indol-3-yl)-propionic acid hydrazides III were easily prepared upon treatment with hydrazine of the corresponding 3-(1H-Indol-3-yl)-propionic acid ethyl esters II that, in their turn, were easily obtained by Fisher esterification of the correspondent commercial 3-(1H-Indol-3-yl)-propionic acids I.

As an example of this general experimental procedure, the experimental procedure for the synthesis of Compound 3 of the invention is described below.

Scheme 1

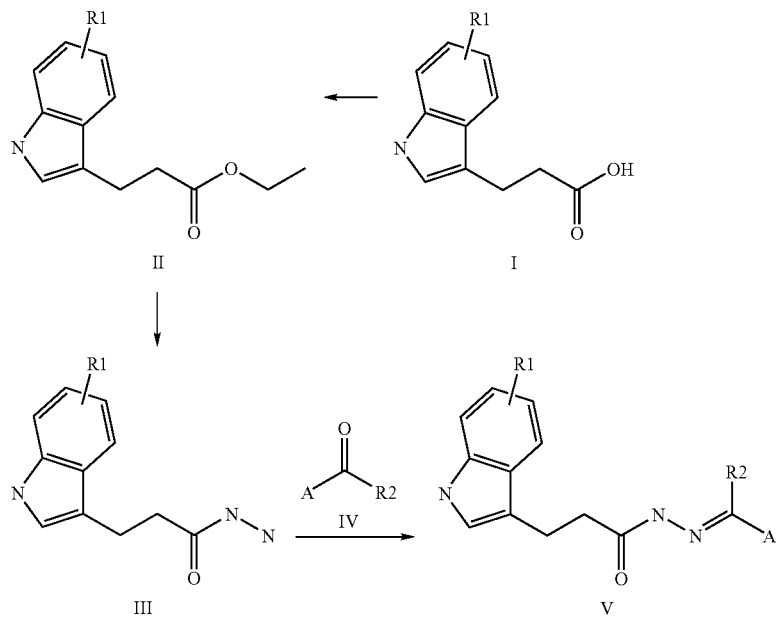

Example of Experimental Procedure

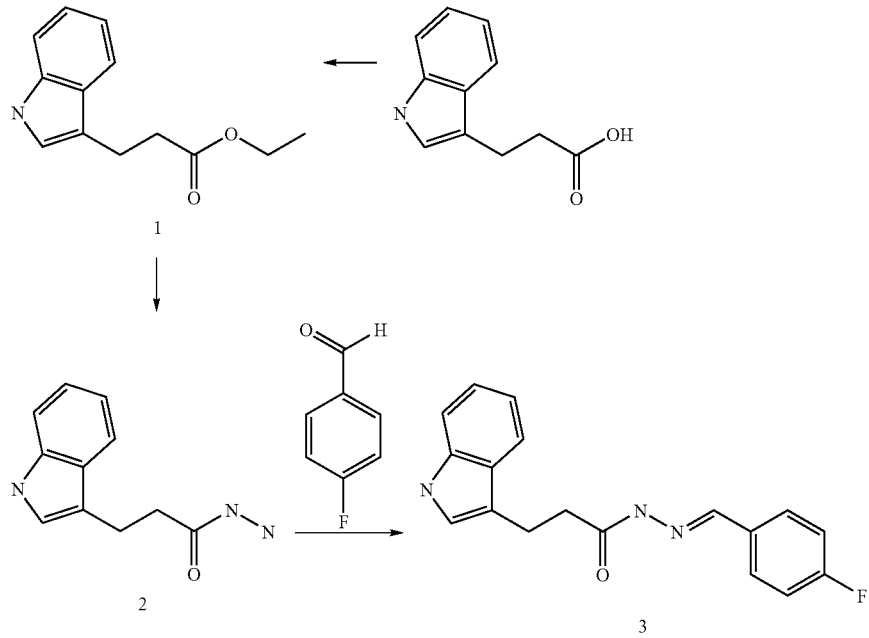

3-(1H-Indol-3-yl)-propionic acid ethyl ester (Intermediate Compound 1)

To a mixture of 3-indolepropionic acid (4.00 g, 1 eq) in ethanol (70 ml), 1 ml of sulphuric acid is added dropwise and the mixture is first refluxed overnight and then evaporated to dryness. The resulting crude residue is dissolved in ethyl acetate and the organic solution is washed with 5% aqueous sodium bicarbonate, water, dried over $MgSO_4$, filtered and finally evaporated to dryness, to afford the title compound as a yellow solid (4.30 g, 95% yield), which is used as such for the next step.

3-(1H-Indol-3-yl)-propionic acid hydrazide (Intermediate Compound 2)

A solution of 3-(1H-Indol-3-yl)-propionic acid ethyl ester (4.30 g, 1 eq) and hydrazine hydrate (~9.6 ml, 10 eq) in ethanol (70 ml) is heated at 60° C. overnight. The reaction mixture is concentrated under reduced pressure and diluted with methylene chloride. The new organic solution is washed with water, dried over $MgSO_4$, filtered and evaporated to dryness, to afford the title compound as white solid (3.9 g, 98% yield), which is used as such for the next step.

3-(1H-Indol-3-yl)-propionic acid [1-(4-fluoro-phenyl)-meth-(E)-ylidene]-hydrazide (Compound 3 of the Invention)

A solution of 3-(1H-Indol-3-yl)-propionic acid hydrazide (0.300 g, 1 eq) and 4-fluorobenzaldehyde (0.183 g, 1 eq) in toluene (7 ml) is refluxed overnight and then evaporated to dryness, to afford 0.450 g of white product that is purified by flash chromatography using neutral alumina and eluting with 1% methanol in chloroform (0.269 g, 59% yield).

In analogy herewith the following compounds were prepared:

3-(1H-Indol-3-yl)-propionic acid [1-phenyl-meth-(E)-ylidene]-hydrazide (Compound 3A)

LC-ESI-HRMS of [M+H]+ shows 292.1436 Da. Calc. 292.144987 Da, dev.-4.7 ppm. M.p. 169.8-171.2 C.°.

3-(1H-Indol-3-yl)-propionic acid [1-(4-methoxy-phenyl)-meth-(E)-ylidene]-hydrazide (Compound 3B)

LC-ESI-HRMS of [M+H]+ shows 322.1554 Da. Calc. 322.155552 Da, dev.-0.5 ppm. M.p. 168.3-169.7° C.

3-(1H-Indol-3-yl)-propionic acid [1-(3-fluoro-phenyl)-meth-(E)-ylidene]-hydrazide (Compound 3C)

LC-ESI-HRMS of [M+H]+ shows 310,1348 Da. Calc. 310,135565 Da, dev.-2,5 ppm.

3-(1H-Indol-3-yl)-propionic acid [1-thiophen-3-yl-meth-(E)-ylidene]-hydrazide (Compound 3D)

LC-ESI-HRMS of [M+H]+ shows 298.102 Da. Calc. 298.101408 Da, dev. 2 ppm. M.p. 145.5-148.1° C.

3-(1H-Indol-3-yl)-propionic acid [1-(2-fluoro-phenyl)-meth-(E)-ylidene]-hydrazide (Compound 3E)

LC-ESI-HRMS of [M+H]+ shows 310.1346 Da. Calc. 310.135565 Da, dev.-3.1 ppm. M.p. 118-123° C.

3-(1H-Indol-3-yl)-propionic acid [1-thiophen-2-yl-meth-(E)-ylidene]-hydrazide (Compound 3F)

LC-ESI-HRMS of [M+H]+ shows 298.102 Da. Calc. 298.101408 Da, dev. 2 ppm. M.p. 146.5-149.4° C.

3-(1H-Indol-3-yl)-propionic acid [1-(4-chloro-phenyl)-meth-(E)-ylidene]-hydrazide (Compound 3G)

LC-ESI-HRMS of [M+H]+ shows 326.1057 Da. Calc. 326.106015 Da, dev.-1 ppm. M.p. 201.5-202.5° C.

3-(1H-Indol-3-yl)-propionic acid [1-cyclohexyl-meth-(E)-ylidene]-hydrazide (Compound 3H)

LC-ESI-HRMS of [M+H]+ shows 298.1926 Da. Calc. 298.191937 Da, dev. 2.2 ppm.

3-(5-Fluoro-1H-indol-3-yl)-propionic acid [1-phenyl-meth-(E)-ylidene]-hydrazide (Compound 3I)

LC-ESI-HRMS of [M+H]+ shows 310.1349 Da. Calc. 310.135565 Da, dev.-2.1 ppm. M.p. 171.2-173.9° C.

3-(5-Fluoro-1H-indol-3-yl)-propionic acid [1-(2-fluoro-phenyl)-meth-(E)-ylidene]-hydrazide (Compound 3J)

LC-ESI-HRMS of [M+H]+ shows 328.1245 Da. Calc. 328.126143 Da, dev.-5 ppm. M.p. 132.8-134.0° C.

3-(1H-Indol-3-yl)-propionic acid [1-phenyl-eth-(E)-ylidene]-hydrazide (Compound 3K)

LC-ESI-HRMS of [M+H]+ shows 306.1598 Da. Calc. 306.160637 Da, dev.-2.7 ppm. M.p. 156.2-158.2° C.

3-(1H-Indol-3-yl)-propionic acid [3,4-dihydro-2H-naphthalen-(1E)-ylidene]-hydrazide (Compound 3L)

LC-ESI-HRMS of [M+H]+ shows 332.1772 Da. Calc. 332.176287 Da, dev. 2.7 ppm. M.p. 119.3-120.2° C.

3-(5-Fluoro-1H-indol-3-yl)-propionic acid [1-(4-fluoro-phenyl)-meth-(E)-ylidene]-hydrazide (Compound 3M)

LC-ESI-HRMS of [M+H]+ shows 328.1263 Da. Calc. 328.126143 Da, dev. 0.5 ppm. M.p. 213.8-215.3° C.

3-(1H-Indol-3-yl)-propionic acid [3-methyl-4-oxo-4H-naphthalen-(1Z)-ylidene]-hydrazide (Compound 3N)

LC-ESI-HRMS of [M+H]+ shows 358.1567 Da. Calc. 358.155552 Da, dev. 3.2 ppm. M.p. 248.6-249.5° C.

Example 2

Biological Activity

Figure 1B:
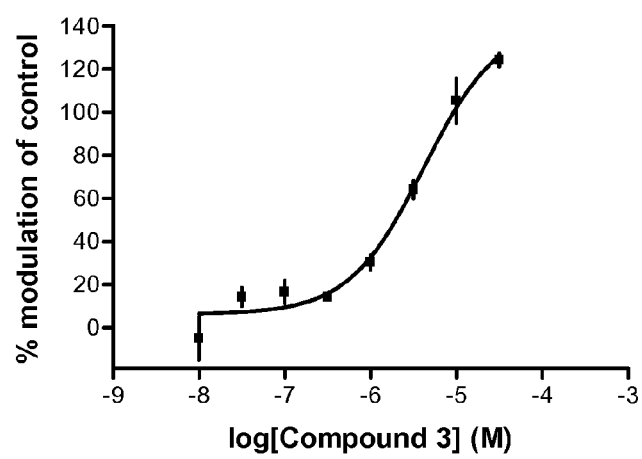

In this example the positive modulation of wild-type nAChR α7 receptors by Compound 3 (FIGS. 1A and 1B) was determined using nAChR α7 receptors heterologously expressed in *Xenopus laevis* oocytes.

The electrical current through the nAChR α7 channel was measured using conventional two-electrode voltage clamp and nAChR α7 currents were activated by applying pulses of agonist-containing solution onto the nAChR α7 expressing oocyte.

In brief, the oocytes were placed in a recording chambers and continuously superfused with an Oocyte Ringer (OR) solution containing 90 mM NaCl, 2.5 mM KCl, 2.5 mM $CaCl_2$, 1 mM $MgCl_2$ and 5 mM HEPES (pH adjusted to 7.4). The oocytes were clamped at −60 mV and currents were induced by applying 20 s pulses of 100 μM acetylcholine dissolved in OR. The intervals between the acetylcholine applications were 5 minutes, during which the oocytes were washed with OR. The first three applications were control applications to insure a constant response level of 100 μM acetylcholine. For the subsequent 8 test applications, increasing concentrations (0.01-31.6 μM) of Compound 3 was applied 30 s before and during the acetylcholine (100 μM) application, which caused a robust increase in the acetylcholine-induced current amplitude.

The positive modulation in the presence of Compound 3 was calculated as (test-control)/control*100% and the concentration response curve for this positive modulation was fitted to the sigmoidal logistic equation: $I=I_{max}/(1+(EC_{50}/[compound])^n)$, where $I_{max}$ represents the maximal modulation of the control response, $EC_{50}$ is the concentration causing a half maximal response, and n is the slope coefficient.

The calculated $EC_{50}$ value and $I_{max}$ value for Compound 3 were 4.1 μM and 140%, respectively.

The invention claimed is:
1. An N-acylhydrazone derivative represented by Formula I

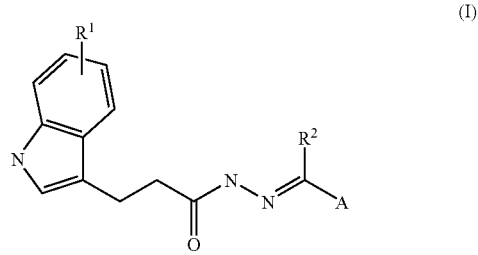

(I)

a stereoisomer thereof or a mixture of its stereoisomers, or
  a pharmaceutically acceptable salt thereof, wherein
$R^1$ represents hydrogen; and
A represents
  a cycloalkyl group; or
  a thienyl group;
  or A together with $R^2$, together with the carbon atom to which they are attached, form a naphthalene or hydrogenated naphthalene ring, which naphthalene and hydrogenated naphthalene are optionally substituted one or more times with substituents selected from alkyl and oxo; and $R^2$ represents hydrogen or alkyl; or $R^2$ together with A, and together with the carbon atom to which they are attached, form a naphthalene or hydrogenated naphthalene ring, which naphthalene and hydrogenated naphthalene are optionally substituted one or more times with substituents selected from alkyl and oxo.

2. The N-acylhydrazone derivative according to claim 1, a stereoisomer thereof or a mixture of its stereoisomers, or a pharmaceutically acceptable salt thereof, wherein $R^2$ together with A, and together with the carbon atom to which they are attached, form a naphthalene or hydrogenated naphthalene ring, which naphthalene and hydrogenated naphthalene are optionally substituted one or more times with substituents selected from alkyl, and in particular methyl, and oxo.

3. The N-acylhydrazone derivative according to claim 1, which is 3-(1H-Indol-3-yl)-propionic acid [1-thiophen-3-yl-meth-(E)-ylidene]-hydrazide;

3-(1H-Indol-3-yl)-propionic acid [1-cyclohexyl-meth-(E)-ylidene]-hydrazide;

3-(1H-Indol-3-yl)-propionic acid [3,4-dihydro-2H-naphthalen-(1E)-ylidene]-hydrazide; or 3-(1H-Indol-3-yl)-propionic acid [3-methyl-4-oxo-4H-naphthalen-(1Z)-ylidene]-hydrazide;

a stereoisomer thereof or a mixture of its stereoisomers, or a pharmaceutically acceptable salt thereof.

4. A pharmaceutical composition comprising:

a therapeutically effective amount of an N-acylhydrazone derivative of claim 1, a stereoisomer thereof or a mixture of its stereoisomers, or a pharmaceutically-acceptable addition salt thereof;

together with at least one pharmaceutically-acceptable carrier or diluent.

5. A composition comprising:

0.1 to 500 mg of an N-acyl derivative of claim 1, a stereoisomer thereof or a mixture of its stereoisomers, or a pharmaceutically-acceptable acid addition salt thereof; and at least one pharmaceutically-acceptable carrier or diluent.

6. A composition comprising:

to 100 mg of an N-acyl derivative of claim 1, a stereoisomer thereof or a mixture of its stereoisomers, or a pharmaceutically-acceptable acid addition salt thereof; and at least one pharmaceutically-acceptable carrier or diluent.

7. A composition comprising:

to 10 mg of an N-acyl derivative of claim 1, a stereoisomer thereof or a mixture of its stereoisomers, or a pharmaceutically-acceptable acid addition salt thereof; and at least one pharmaceutically-acceptable carrier or diluent.

8. The N-acylhydrazone derivative according to claim 1, which is 3-(1H-Indol-3-yl)-propionic acid [1-thiophen-3-yl-meth-(E)-ylidene]-hydrazide or a pharmaceutically acceptable salt thereof.

9. The N-acylhydrazone derivative according to claim 1, which is 3-(1H-Indol-3-yl)-propionic acid [1-cyclohexyl-meth-(E)-ylidene]-hydrazide or a pharmaceutically acceptable salt thereof.

10. The N-acylhydrazone derivative according to claim 1, which is 3-(1H-Indol-3-yl)-propionic acid [3,4-dihydro-2H-naphthalen-(1E)-ylidene]-hydrazide or a pharmaceutically acceptable salt thereof.

11. The N-acylhydrazone derivative according to claim 1, which is 3-(1H-Indol-3-yl)-propionic acid [3-methyl-4-oxo-4H-naphthalen-(1Z)-ylidene]-hydrazide or a pharmaceutically acceptable salt thereof.

* * * * *